(12) United States Patent
Goodson, IV et al.

(10) Patent No.: US 6,945,992 B2
(45) Date of Patent: Sep. 20, 2005

(54) SINGLE-PIECE CROWN STENT (75) Inventors: Harry B. Goodson, IV, Fremont, CA (US); Trevor Greenan, Miami, FL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/421,054

(22) Filed: Apr. 22, 2003

(65) Prior Publication Data

US 2004/0215326 A1 Oct. 28, 2004

(51) Int. Cl.⁷ .................................................. A61F 2/06
(52) U.S. Cl. ...................................................... 623/1.13
(58) Field of Search ............................... 623/1.11–1.22

(56) References Cited

U.S. PATENT DOCUMENTS

| | | | | |
|---|---|---|---|---|
| 6,053,940 A | * | 4/2000 | Wijay | 623/1.15 |
| 6,270,524 B1 | * | 8/2001 | Kim | 623/1.15 |
| 6,312,458 B1 | * | 11/2001 | Golds | 623/1.13 |
| 6,428,570 B1 | * | 8/2002 | Globerman | 623/1.15 |
| 2002/0042645 A1 | * | 4/2002 | Shannon | 623/1.13 |
| 2002/0120327 A1 | * | 8/2002 | Cox et al. | 623/1.16 |
| 2002/0183832 A1 | * | 12/2002 | Penn et al. | 623/1.16 |
| 2003/0114921 A1 | * | 6/2003 | Yoon | 623/1.16 |
| 2003/0125797 A1 | * | 7/2003 | Chobotov et al. | 623/1.13 |
| 2003/0130724 A1 | * | 7/2003 | DePalma et al. | 623/1.16 |
| 2003/0181969 A1 | * | 9/2003 | Kugler et al. | 623/1.13 |
| 2003/0225447 A1 | * | 12/2003 | Majercak et al. | 623/1.13 |
| 2004/0044396 A1 | * | 3/2004 | Clerc et al. | 623/1.13 |
| 2004/0068316 A1 | * | 4/2004 | Schaeffer | 623/1.16 |
| 2004/0082990 A1 | * | 4/2004 | Hartley | 623/1.13 |

* cited by examiner

Primary Examiner—Suzette J-J Gherbi (57) ABSTRACT

A stent for a stent-graft includes: a first ring; a second ring; and spring elements coupling the first ring to the second ring, wherein the first ring, the second ring and the spring elements are integral. During maneuvering of the stent-graft through the tortuous human anatomy, the first ring is bent or flexed relative to the second ring. However, the spring elements are distorted to accommodate this bending. Further, since the stent is integral, a graft material only has to be sewn to the second ring minimizing the delivery profile of the stent-graft.

32 Claims, 8 Drawing Sheets

SINGLE-PIECE CROWN STENT

BACKGROUND OF THE INVENTION

1. Field of the Invention

The present invention relates to intra-vascular devices. More particularly, the present invention relates to a stent for treatment of intra-vascular aneurysms.

2. Description of the Related Art

A self-expanding stent-graft typically includes a self-expanding stent and a graft material sewn to the stent. In stent-graft deployment systems, the self-expanding stent-graft is restrained within a sheath. After placement of the stent-graft at the desired location via fluoroscopic guidance, the physician retracts the sheath to deploy the stent-graft, i.e., to expose the stent-graft and allow it to self-expand.

However, the human anatomy is tortuous by nature. Thus, during guidance of the stent-graft to the desired location, the stent-graft is subjected to significant bending and flexing. A conventional stent-graft has practical limits to the allowed amount of bending to avoid damage or destruction to the stent-graft. Avoiding extreme bending or destruction of the stent-graft limits the range of anatomical variation in which the stent-graft can be used.

Further, to guide the stent-graft to the desired location, the stent-graft is compressed within the sheath to have the smallest possible cross-section, i.e., to have the smallest possible stent-graft delivery profile. However, conventional stent-graft designs imposed practical limits on the possible reduction of the stent-graft delivery profile.

SUMMARY OF THE INVENTION

In one embodiment according to the present invention, a stent for a stent-graft includes: a first ring; a second ring; and spring elements coupling the first ring to the second ring, wherein the first ring, the second ring and the spring elements are integral.

During maneuvering of the stent-graft through the tortuous human anatomy, the first ring is bent or flexed relative to the second ring. However, the spring elements are distorted to accommodate this bending.

Further, since the first ring, the second ring and the spring elements of the stent are integral, a graft material only has to be sewn to the second ring. By sewing the graft material only to the second ring, there is less overlap of the graft material and the stent compared to having to sew the graft material to both the first ring and the second ring. Accordingly, use of a stent according to the present invention minimizes the delivery profile of the stent-graft.

Embodiments according to the present invention are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

In accordance with one embodiment of the present invention, a stent 100 (FIGS. 2 and 3) for a stent-graft 200 includes: an upper sinusoidal ring 102; a lower diamond ring 104; and spring elements 106 coupling upper sinusoidal ring 102 to lower diamond ring 104, wherein upper sinusoidal ring 102, lower diamond ring 104, and spring elements 106 are integral.

Figure 2:
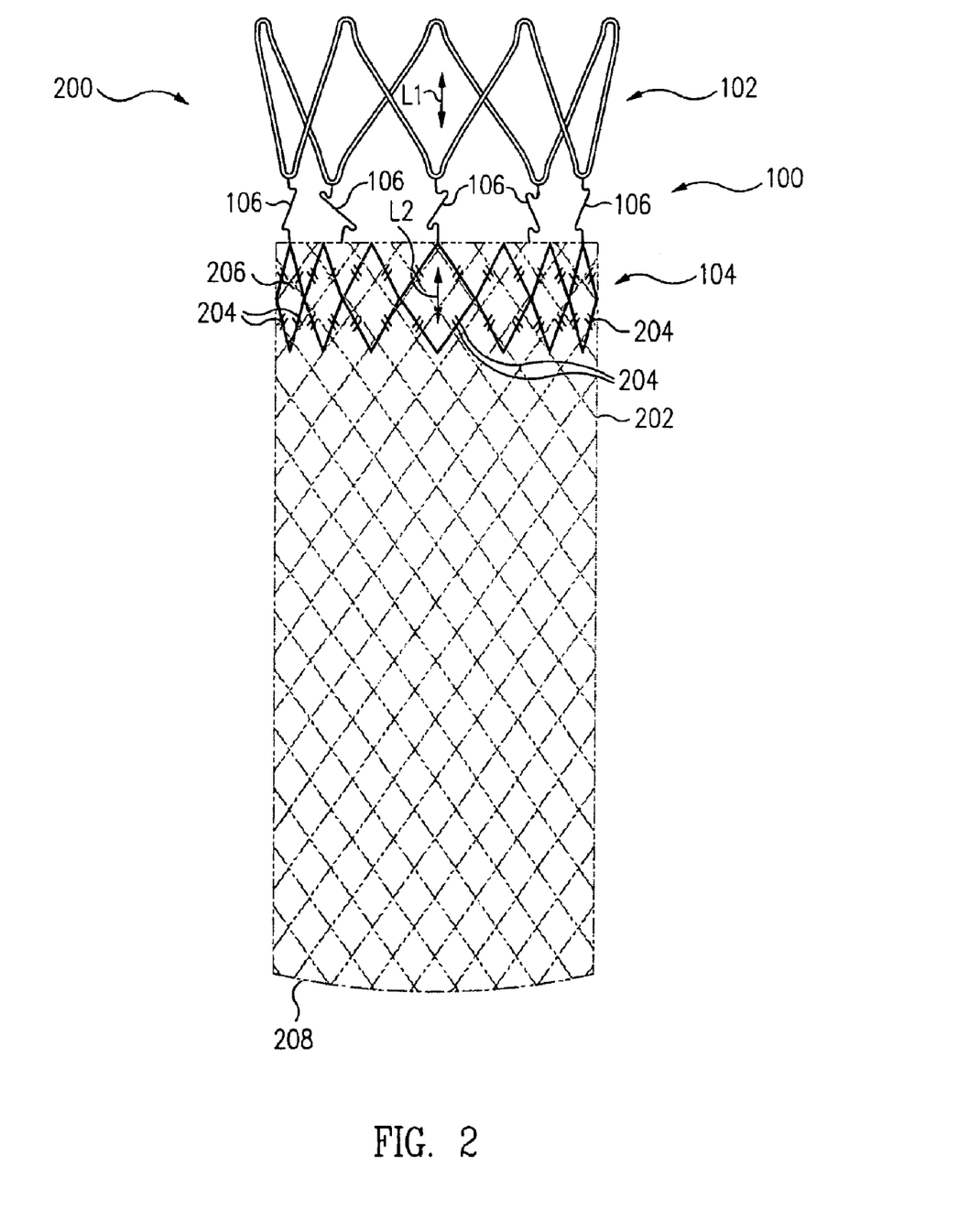
FIG. 2 is a side view of a stent-graft formed with the stent of FIG. 1A.
Figure 3:
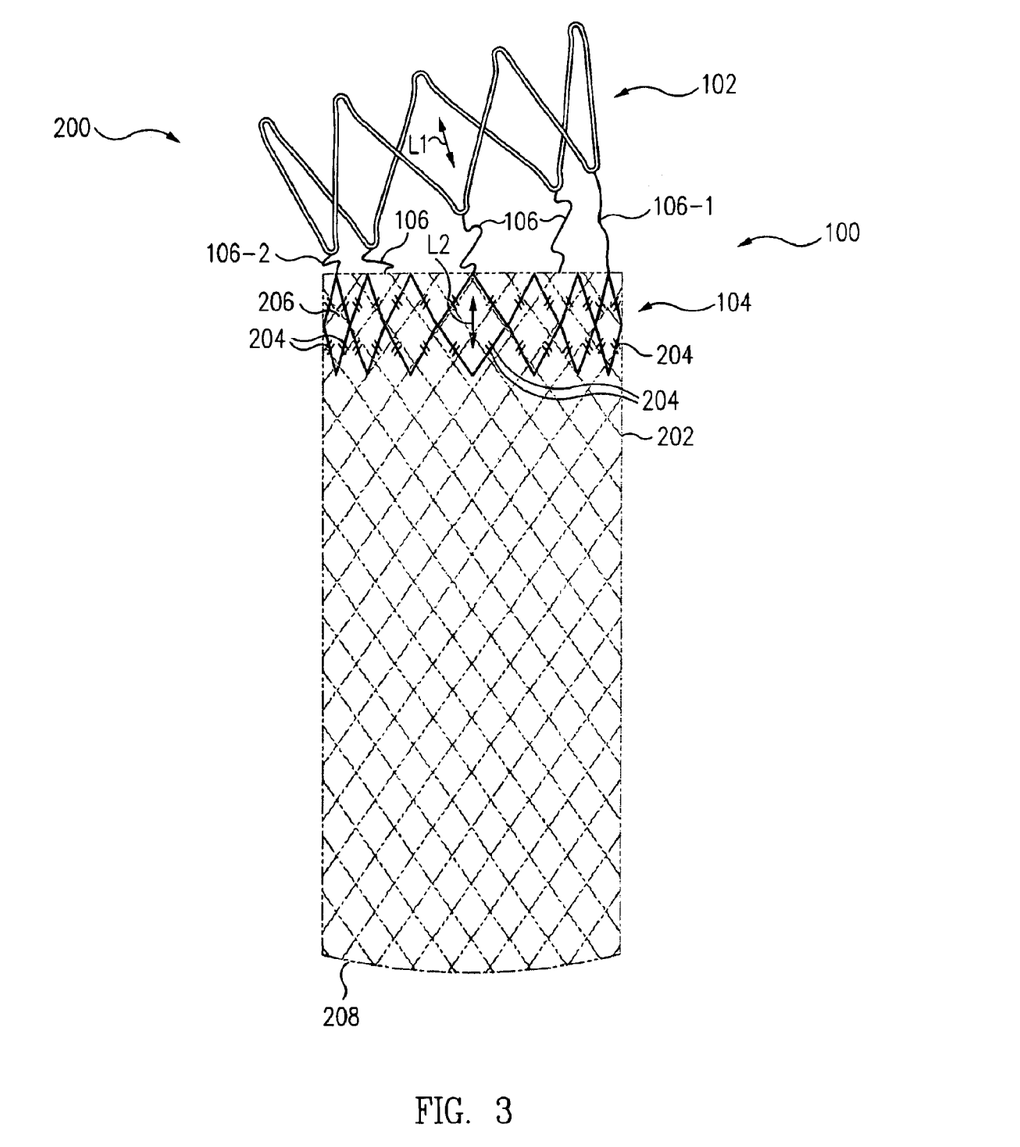
FIG. 3 is a side view of the stent-graft of FIG. 2 with spring elements being bent and distorted.

In one embodiment, during maneuvering stent-graft 200 through the tortuous human anatomy, e.g., from the femoral artery to the abdominal aorta, upper sinusoidal ring 102 is bent or flexed relative to lower diamond ring 104. However, spring elements 106 are distorted to accommodate this bending.

Further, since stent 100 is integral, graft material 202 only has to be sewn to lower diamond ring 104. By sewing graft material 202 only to lower diamond ring 104, there is less overlap of graft material 202 and stent 100 and therefore less thickness of material to be compressed into the sheath compared to having to sew graft material 202 to both upper sinusoidal ring 102 and lower diamond ring 104. Accordingly, use of stent 100 minimizes the delivery profile of stent-graft 200.

Figure 1A:
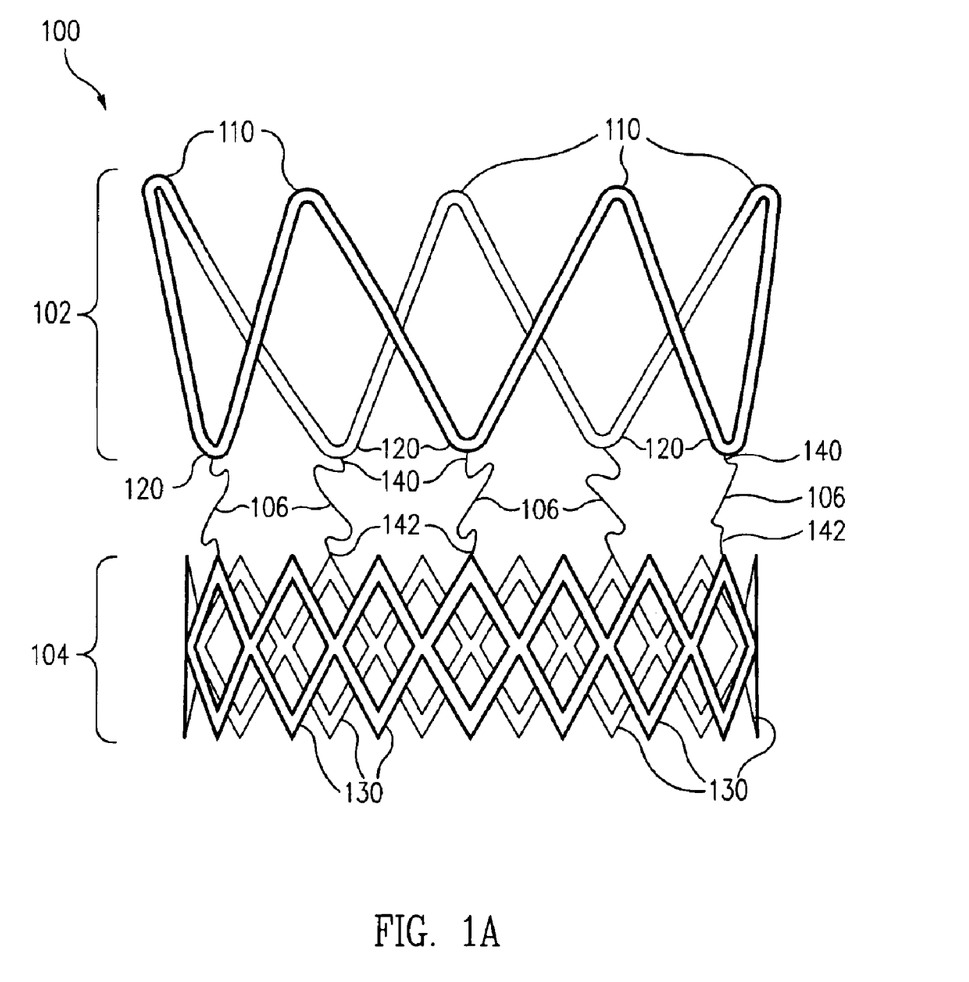
FIGS. 1A, 1B and 1C are side views of various embodiments of a single-piece stent in accordance with the present invention.

More particularly, FIG. 1A is a side view of a single-piece stent 100 in accordance with one embodiment of the present invention. Stent 100 includes an upper sinusoidal ring 102, a lower diamond ring 104, and spring elements 106. Upper sinusoidal ring 102 is sometimes called a first ring or a crown ring due to the shape of upper sinusoidal ring 102. Lower diamond ring 104 is sometimes called a second ring. Spring elements 106 are sometimes called means for bending.

Upper sinusoidal ring 102 has a sinusoidal shape, i.e., is a series of peaks 110 and valleys 120. Lower diamond ring 104 is a series of connected diamond shaped structures 130.

Spring elements 106 couple upper sinusoidal ring 102 to lower diamond ring 104. As shown in FIG. 1A, each valley 120 is coupled to an upper, e.g., first, end 140 of a corresponding spring element 106. However, in an alternative embodiment, spring elements 106 are not coupled to every valley 120, e.g., are coupled only to every other valley 120 or at least to one valley 120.

Further, lower, e.g., second, ends 142 of spring elements 106 are directly coupled to every third diamond shaped structure 130, i.e., two diamond shaped structures 130 not directly coupled to spring elements 106 are between diamond shaped structures 130 which are directly coupled to spring elements 106. More particularly, the number of diamond shaped structures 130 of lower diamond ring 104 is greater than the number of valleys 120 of upper sinusoidal ring 102, e.g., there are three diamond shaved structures 130 for every valley 120 as illustrated in FIG. 1A. However, in other embodiments, more or less of diamond shaped structures 130 are directly coupled to spring elements 106.

Further, spring elements 106 are flexible and resilient allowing upper sinusoidal ring 102 to be bent or flexed relative to lower diamond ring 104 yet cause upper sinusoidal ring 102 to be returned to its original position as discussed in greater detail below with reference to FIG. 3.

In accordance with this embodiment, stent 100 is integral, sometimes called a single-piece, i.e., upper sinusoidal ring 102, lower diamond ring 104, and spring elements 106 are a single piece (cut from a single tube) and not a plurality of separate pieces connected together.

For example, a single tubular piece of memory metal is cut with a laser in an inert atmosphere, e.g., an argon cut, to form stent 100. However, stent 100 is formed using other techniques such as machining in another embodiment.

In one embodiment, a 0.125 or 0.187 inch outside diameter tube of nickel titanium alloy, e.g., nitinol, is argon cut and expanded, e.g., to have an outer diameter of 28 mm, 30 mm, 32 mm or 40 mm, to form stent 100. Further, in one embodiment, after cutting, the tube of nickel titanium alloy is expanded using a series of expansion steps where the tube of nickel titanium alloy is sequentially expanded and heated, e.g., three or four times, to expand the tube of nickel titanium alloy to the desired outer diameter.

In one embodiment, the tube is: 1) expanded and held at 470° C. for 2 minutes; 2) further expanded and held at 470° C. for 2 minutes; and 3) further expanded to have the desired outer diameter and held at 525° C. for 2 minutes. In another embodiment, the tube is: 1) expanded and held at 505° C. for 2 minutes; 2) further expanded and held at 505° C. for 2 minutes; and 3) further expanded to have the desired outer diameter and held at 505° C. for 2 minutes.

Figure 1B:
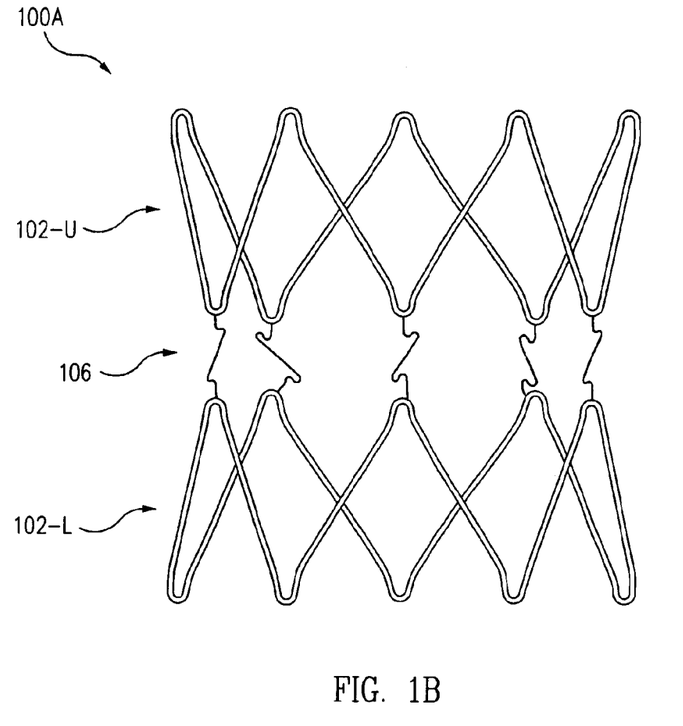

FIG. 1B is a side view of a single-piece stent 100A in accordance with one embodiment of the present invention. Stent 100A includes an upper sinusoidal ring 102-U, a lower sinusoidal ring 102-L, and spring elements 106. Upper sinusoidal ring 102-U and lower sinusoidal ring 102-L are similar to one another and are sometimes called a first ring and a second ring, respectively, or crown rings due to their shape.

Upper sinusoidal ring 102-U and lower sinusoidal ring 102-L have a sinusoidal shape, i.e., are a series of peaks and valleys. Spring elements 106 couple upper sinusoidal ring 102-U to lower sinusoidal ring 102-L.

Figure 1C:
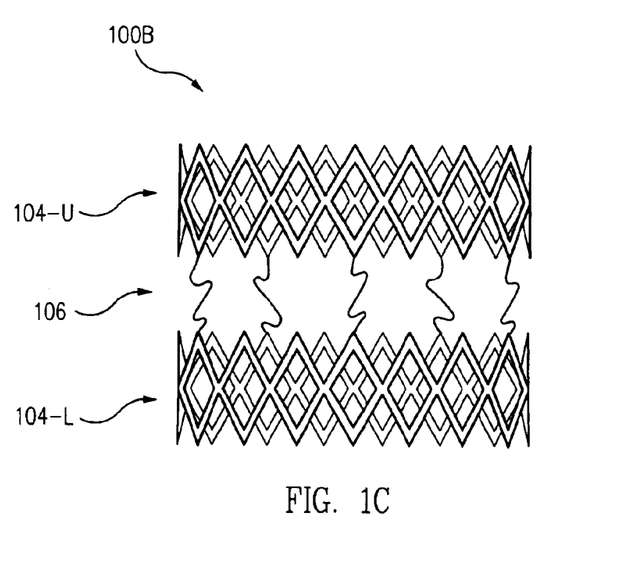

FIG. 1C is a side view of a single-piece stent 100B in accordance with one embodiment of the present invention. Stent 100B includes an upper diamond ring 104-U, a lower diamond ring 104-L, and spring elements 106. Upper diamond ring 104-U and lower diamond ring 104-L are similar to one another and are sometimes called a first ring and a second ring, respectively.

Upper diamond ring 104-U and lower diamond ring 104-L are a series of connected diamond shaped structures. Spring elements 106 couple upper diamond ring 104-U to lower diamond ring 104-L.

FIG. 2 is a side view of a stent-graft 200 in its relaxed state formed with stent 100 of FIG. 1A in accordance with one embodiment of the present invention. As shown in FIG. 2, a graft material 202 is sewn by sutures 204 to lower diamond ring 104 of stent 100. Since stent 100 is integral, graft material 202 only has to be sewn to lower diamond ring 104.

In contrast, the graft material of a conventional stent-graft formed with individual stent elements had to be sewn to each of the individual stent elements. Since graft material 202 is only sewn to lower diamond ring 104, production sewing time is saved.

Further, by sewing graft material 202 only to lower diamond ring 104, less sutures 204 are used as compared to a conventional stent-graft in which the graft material had to be sewn to each of the individual stent elements again saving production sewing time.

Still further, by sewing graft material 202 only to lower diamond ring 104, there is less overlap of graft material 202 and stent 100 compared to having to sew the graft material to each individual stent element as in a convention stent-graft. By minimizing overlap of stent 100 and graft material 202, there is less thickness of material to be compressed into the sheath. Accordingly, use of stent 100 minimizes the delivery profile of stent-graft 200.

However, in another embodiment, graft material 202 is sewn to both lower diamond ring 104 and upper sinusoidal ring 102. In yet another embodiment, stent 100 is inverted such that sinusoidal ring 102 is below diamond ring 104 in the view of FIG. 2 and graft material 202 is sewn to sinusoidal ring 102.

Referring still to the embodiment illustrated in FIG. 2, a proximal end 206, sometimes called first end, of graft material 202 is sewn to lower diamond ring 104. Graft material 202 extends downwards, e.g., in a first direction, from lower diamond ring 104 and more generally from stent 100 to a distal end 208, sometimes called a second end of graft material 202.

In one embodiment, upper sinusoidal ring 102 provides fixation above the renal arteries. Further, lower diamond ring 104 provides sealing at proximal end 206 of graft material 202 by pressing proximal end 206 into contact with the body lumen in which stent-graft 200 is deployed. Still further, during positioning of stent-graft 200 within the human body, spring elements 106 are bent and distorted as discussed below with reference to FIG. 3.

FIG. 3 is a side view of stent-graft 200 of FIG. 2 with spring elements 106 being bent and distorted. Referring now to FIGS. 2 and 3 together, initially an upper longitudinal axis L1 of upper sinusoidal ring 102 is parallel to and aligned with a lower longitudinal axis L2 of lower diamond ring 104 as shown in FIG. 2. Stated another way, stent-graft 200 is in its relaxed state in FIG. 2, i.e., no bending force is being applied to stent-graft 200. Although the term relaxed state is used herein, it is to be understood that stent-graft 200 may be radially compressed, e.g., radially constrained within a sheath, while being in its relaxed state.

Although the terms parallel, aligned, and similar terms are used herein with reference to certain elements, it is understood that the elements may not be exactly parallel or aligned, but only substantially parallel or aligned to accepted manufacturing tolerances.

However, during maneuvering through the tortuous human anatomy, bending force applied to stent-graft 200 causes (and allows) upper sinusoidal ring 102 to be bent or flexed relative to lower diamond ring 104. Accordingly, as shown in FIG. 3, upper longitudinal axis L1 of upper sinusoidal ring 102 becomes unaligned and unparallel with lower longitudinal axis L2 of lower diamond ring 104. However, spring elements 106 are distorted to accommodate this bending.

More particularly, spring elements 106 are readily stretched between upper sinusoidal ring 102 and lower diamond ring 104. To illustrate, a first spring element 106-1 of the plurality of spring elements 106 is stretched as the spacing between the respective connected portions of upper sinusoidal ring 102 and lower diamond ring 104 increases due to the flexing or bending of upper sinusoidal ring 102 relative to lower diamond ring 104.

Further, spring elements 106 are readily compressed between upper sinusoidal ring 102 and lower diamond ring 104. To illustrate, a second spring element 106-2 of the plurality of spring elements 106 is compressed as the spacing between the respective connected portions of upper sinusoidal ring 102 and lower diamond ring 104 decreases due to the flexing or bending of upper sinusoidal ring 102 relative to lower diamond ring 104.

In one embodiment, upper sinusoidal ring 102 is bent back and forth up to 180° relative to lower diamond ring 104 such that upper longitudinal axis L1 of upper sinusoidal ring 102 moves up to ±90° from lower longitudinal axis L2 of lower diamond ring 104. In accordance with this embodiment, all or most of the bending occurs in spring elements 106 without collapse of either upper sinusoidal ring 102, lower diamond ring 104 or damage to stent-graft 200.

Accordingly, stent-graft 200 is readily maneuvered through the tortuous human anatomy. Further, when the bending force is no longer applied to or removed from stent-graft 200, e.g., stent-graft 200 has reached its desired location, spring elements 106 return stent-graft 200 back to its relaxed state as shown in FIG. 2 due to the resiliency of spring elements 106.

Figure 4:
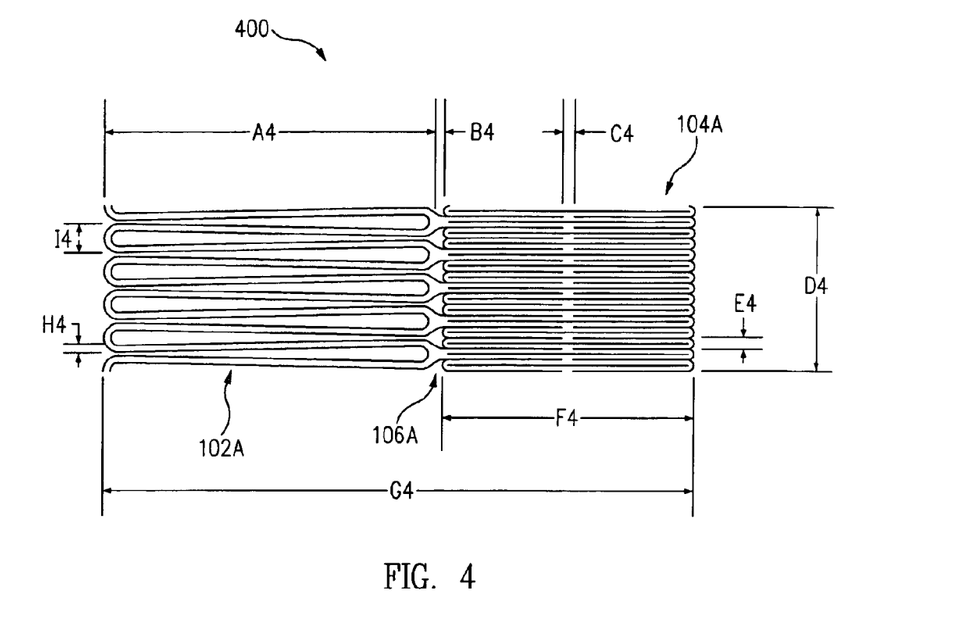
FIGS. 4, 5, 6A, 6B, 7, 8, 9 and 10 are flat layout plan views of various embodiments of laid flat tube patterns for a single-piece stent in accordance with the present invention.

FIG. 4 is a flat layout plan view of a laid flat tube pattern 400 for a single-piece stent. Referring now to FIG. 4, spring elements 106A consist of straight connectors extending between upper sinusoidal ring 102A and lower diamond ring 104A. Accordingly, spring elements 106A are sometimes said to be in a straight line pattern.

Illustrative specifications for the various features illustrated in FIG. 4 are set forth below in Table 1.

TABLE 1

| FEATURE | SPECIFICATION | UNIT |
| --- | --- | --- |
| A4 | 0.750 | Inch |
| B4 | 0.019 | Inch |
| C4 | 0.030 | Inch |
| D4 | 0.393 | Inch |
| E4 | 0.026 | Inch |
| F4 | 0.559 | Inch |
| G4 | 1.328 | Inch |
| H4 | 0.018 | Inch |
| I4 | 0.070 | Inch |

The ratio of height A4 of upper sinusoidal ring 102A and height B4 of spring elements 106A is about 40:1, i.e., height A4 (0.750) of upper sinusoidal ring 102A is about 40 times as great as height B4 (0.019). The ratio of height B4 of spring elements 106A and height F4 of lower diamond ring 104A is about 1:30. The ratio of height A4 of upper sinusoidal ring 102A and height F4 of lower diamond ring 104A is about 4:3. The ratio of height A4 of upper sinusoidal ring 102A and height B4 of spring elements 106A and height F4 of lower diamond ring 104A is about 40:1:30.

Figure 5:
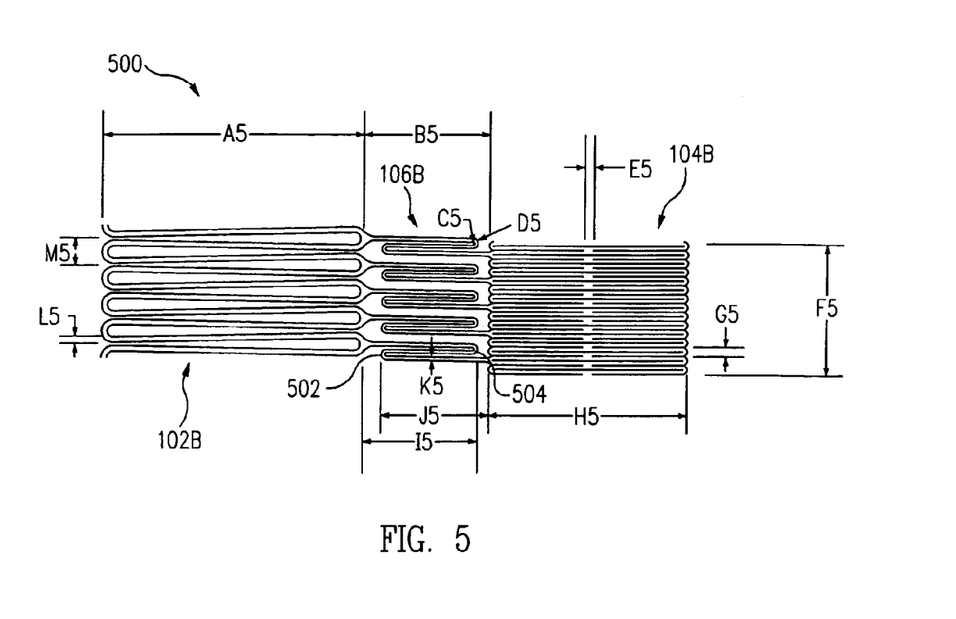

FIG. 5 is a flat layout plan view of a laid flat tube pattern 500 for a single-piece stent showing another embodiment according to the present invention. Referring now to FIG. 5, spring elements 106B consist of S-shaped connectors extending between upper sinusoidal ring 102B and lower diamond ring 104B. More particularly, each spring element 106B consists of two opposing 180 degree bends 502, 504. Accordingly, spring elements 106B are sometimes said to be in an S-pattern. As used herein, an S-pattern includes two opposing bends. Thus, an S-pattern or S-shaped structure is similar in shape to the letter "S" or the mirror image of the letter "S".

Illustrative specifications for the various features illustrated in FIG. 5 are set forth below in Table 2.

TABLE 2

| FEATURE | SPECIFICATION | UNIT |
| --- | --- | --- |
| A5 | 0.754 | Inch |
| B5 | 0.309 | Inch |
| C5 | R0.005 | Inch |
| D5 | R0.015 | Inch |
| E5 | 0.030 | Inch |
| F5 | 0.393 | Inch |
| G5 | 0.026 | Inch |
| H5 | 0.559 | Inch |
| I5 | 0.270 | Inch |
| J5 | 0.247 | Inch |
| K5 | 0.010 | Inch |
| L5 | 0.022 | Inch |
| M5 | 0.074 | Inch |

The ratio of height A5 of upper sinusoidal ring 102B and height B5 of spring elements 106B is about 5:2. The ratio of height B5 of spring elements 106B and height H5 of lower diamond ring 104B is about 5:9. The ratio of height A5 of upper sinusoidal ring 102B and height H5 of lower diamond ring 104B is about 25:18. The ratio of height A5 of upper sinusoidal ring 102B and height B5 of spring elements 106B and height H5 of lower diamond ring 104B is about 25:10:18.

Figure 6A:
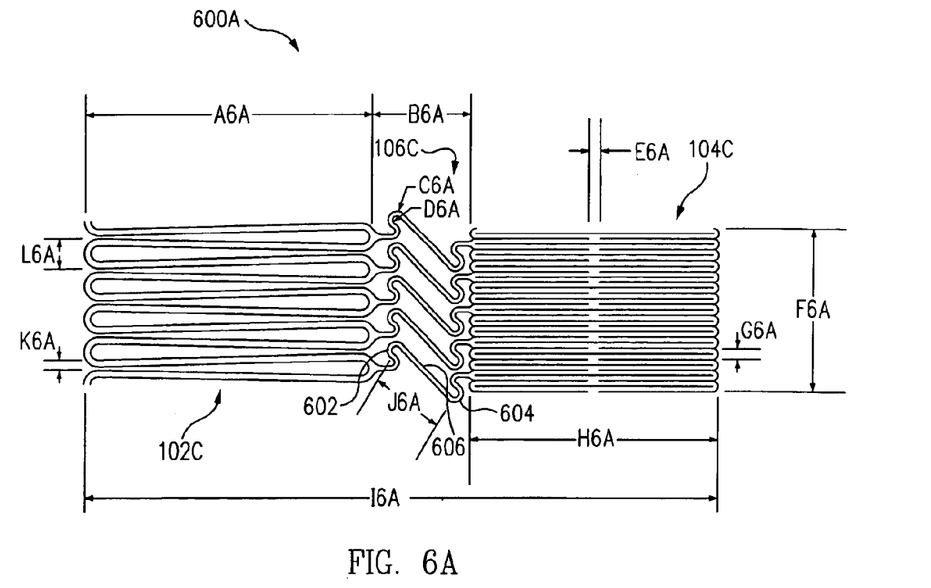

FIG. 6A is a flat layout plan view of a laid flat tube pattern 600A for a single-piece stent showing another embodiment according to the present invention. Referring now to FIG. 6A, spring elements 106C extend between upper sinusoidal ring 102C and lower diamond ring 104C. Spring elements 106C consist of: first S-shaped connectors 602; second S-shaped connectors 604; and straight struts 606 extending between connectors 602, 604. Accordingly, each spring element 106C is sometimes said to be in a pattern of two S-patterns connected by a straight strut.

Illustrative specifications for the various features illustrated in FIG. 6A in accordance with one embodiment are set forth below in Table 3.

TABLE 3

| FEATURE | SPECIFICATION | UNIT |
| --- | --- | --- |
| A6A | 0.754 | Inch |
| B6A | 0.247 | Inch |
| C6A | R0.020 | Inch |
| D6A | R0.010 | Inch |
| E6A | 0.030 | Inch |
| F6A | 0.393 | Inch |
| G6A | 0.026 | Inch |
| H6A | 0.559 | Inch |
| I6A | 1.560 | Inch |
| J6A | 0.184 | Inch |
| K6A | 0.022 | Inch |
| L6A | 0.074 | Inch |

The ratio of height A6A of upper sinusoidal ring 102C and height B6A of spring elements 106C is about 3:1. The ratio of height B6A of spring elements 106C and height H6A of lower diamond ring 104C is about 4:9. The ratio of height A6A of upper sinusoidal ring 102C and height H6A of lower diamond ring 104C is about 4:3. The ratio of height A6A of upper sinusoidal ring 102C and height B6A of spring elements 106C and height H6A of lower diamond ring 104C is about 12:4:9.

Illustrative specifications for the various features illustrated in FIG. 6A in accordance with other embodiments are set forth below in Table 4.

TABLE 4

| FEATURE | SPECIFICATION | UNIT |
| --- | --- | --- |
| A6A | 0.754 | Inch |
| B6A | 0.247 | Inch |
| C6A | R0.020 | Inch |
| D6A | R0.010* | Inch |
|  | (R0.0075**) |  |
|  | (R0.0125***) |  |
| E6A | 0.025 | Inch |
| F6A | 0.393 | Inch |
| G6A | 0.026 | Inch |
| H6A | 0.539 | Inch |
| I6A | 1.540 | Inch |
| J6A | 0.184 | Inch |
| K6A | 0.022 | Inch |
| L6A | 0.074 | Inch |

*When strut 606 is 0.0100 inch thick.
**When strut 606 is 0.0125 inch thick.
***When strut 606 is 0.0075 inch thick.

With respect to Table 4, the ratio of height A6A of upper sinusoidal ring 102C and height B6A of spring elements 106C is about 3:1. The ratio of height B6A of spring elements 106C and height H6A of lower diamond ring 104C is about 5:11. The ratio of height A6A of upper sinusoidal ring 102C and height H6A of lower diamond ring 104C is about 15:11. The ratio of height A6A of upper sinusoidal ring 102C and height B6A of spring elements 106C and height H6A of lower diamond ring 104C is about 15:5:11.

Figure 6B:
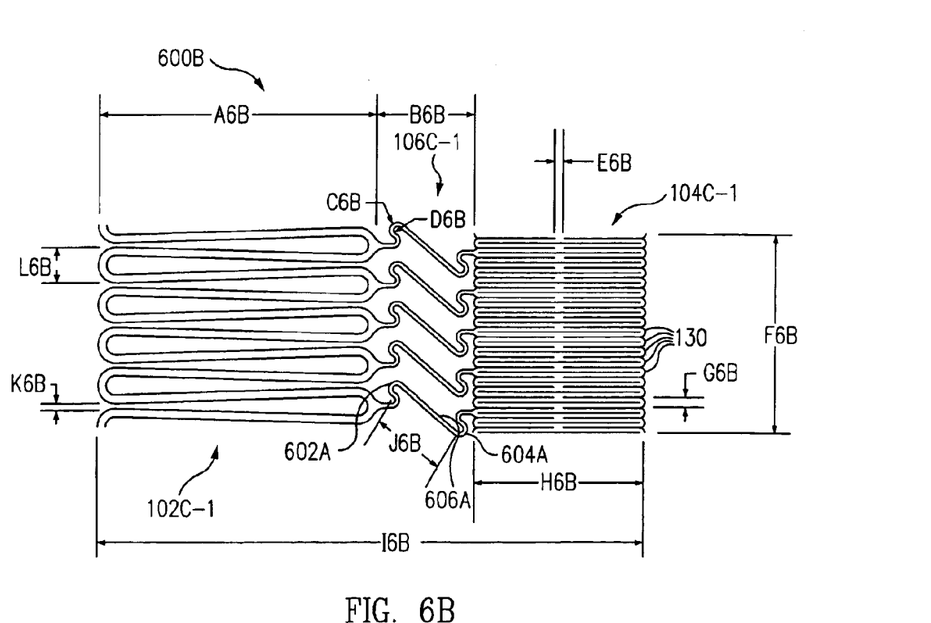

FIG. 6B is a flat layout plan view of a laid flat tube pattern 600B for a single-piece stent showing another embodiment according to the present invention. Referring now to FIG. 6B, spring elements 106C-1 extend between upper sinusoidal ring 102C-1 and lower diamond ring 104C-1. Spring elements 106C-1 consist of: first S-shaped connectors 602A; second S-shaped connectors 604A; and straight struts 606A extending between connectors 602A, 604A. Accordingly, each spring element 106C-1 is sometimes said to be in a pattern of two S-patterns connected by a straight strut.

In accordance with this embodiment, spring elements 106C-1 are directly coupled to every fourth diamond shaped structure 130 of lower diamond ring 104C-1, i.e., three diamond shaped structures 130 not directly coupled to spring elements 106C-1 are between diamond shaped structures 130 which are directly coupled to spring elements 106C-1.

Illustrative specifications for the various features illustrated in FIG. 6B are set forth below in Table 5.

TABLE 5

| FEATURE | SPECIFICATION | UNIT |
| --- | --- | --- |
| A6B | 0.835 | Inch |
| B6B | 0.270 | Inch |
| C6B | R0.020 | Inch |
| D6B | R0.010 | Inch |
| E6B | 0.030 | Inch |
| F6B | 0.578 | Inch |
| G6B | 0.029 | Inch |
| H6B | 0.458 | Inch |
| I6B | 1.563 | Inch |
| J6B | 0.184 | Inch |
| K6B | 0.020 | Inch |
| L6B | 0.100 | Inch |

The ratio of height A6B of upper sinusoidal ring 102C-1 and height B6B of spring elements 106C-1 is about 3:1. The ratio of height B6B of spring elements 106C-1 and height H6B of lower diamond ring 104C-1 is about 4:9. The ratio of height A6B of upper sinusoidal ring 102C-1 and height H6B of lower diamond ring 104C-1 is about 4:3. The ratio of height A6B of upper sinusoidal ring 102C-1 and height B6B of spring elements 106C-1 and height H6B of lower diamond ring 104C-1 is about 12:4:9.

Figure 7:
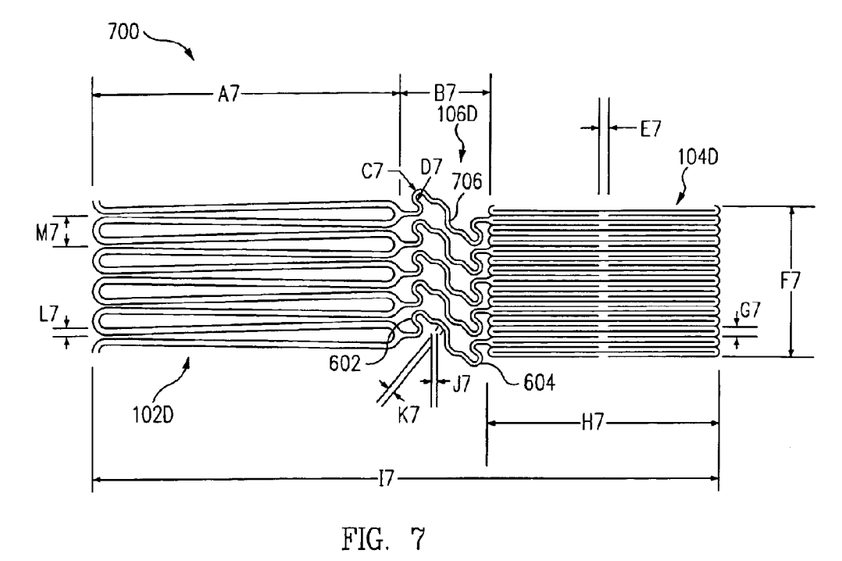

FIG. 7 is a flat layout plan view of a laid flat tube pattern 700 for a single-piece stent showing another embodiment according to the present invention. Referring now to FIGS. 6A and 7 together, spring elements 106C of FIG. 7 are similar to spring elements 106C of FIG. 6A except spring elements 106D (FIG. 7) include wave struts 706 which are different than straight struts 606 (FIG. 6A)

Referring now to FIG. 7, spring elements 106D extend between upper sinusoidal ring 102D and lower diamond ring 104D. Spring elements 106D consist of: first S-shaped connectors 602; second S-shaped connectors 604; and wave struts 706 extending between connectors 602, 604. Wave struts 706 include angulations, i.e., are not straight. Accordingly, each spring element 106D is sometimes said to be in a pattern of two S-patterns connected by a wave strut.

Illustrative specifications for the various features illustrated in FIG. 7 are set forth below in Table 6.

TABLE 6

| FEATURE | SPECIFICATION | UNIT |
| --- | --- | --- |
| A7 | 0.754 | Inch |
| B7 | 0.247 | Inch |
| C7 | R0.020 | Inch |
| D7 | R0.010 | Inch |
| E7 | 0.030 | Inch |
| F7 | 0.393 | Inch |
| G7 | 0.026 | Inch |
| H7 | 0.559 | Inch |
| I7 | 1.560 | Inch |
| J7 | 0.015 | Inch |
| K7 | 0.020 | Inch |
| L7 | 0.022 | Inch |
| M7 | 0.074 | Inch |

The ratio of height A7 of upper sinusoidal ring 102D and height B7 of spring elements 106D is about 3:1. The ratio of height B7 of spring elements 106D and height H7 of lower diamond ring 104D is about 4:9. The ratio of height A7 of upper sinusoidal ring 102D and height H7 of lower diamond ring 104D is about 4:3. The ratio of height A7 of upper sinusoidal ring 102D and height B7 of spring elements 106D and height H7 of lower diamond ring 104D is about 12:4:9.

Figure 8:
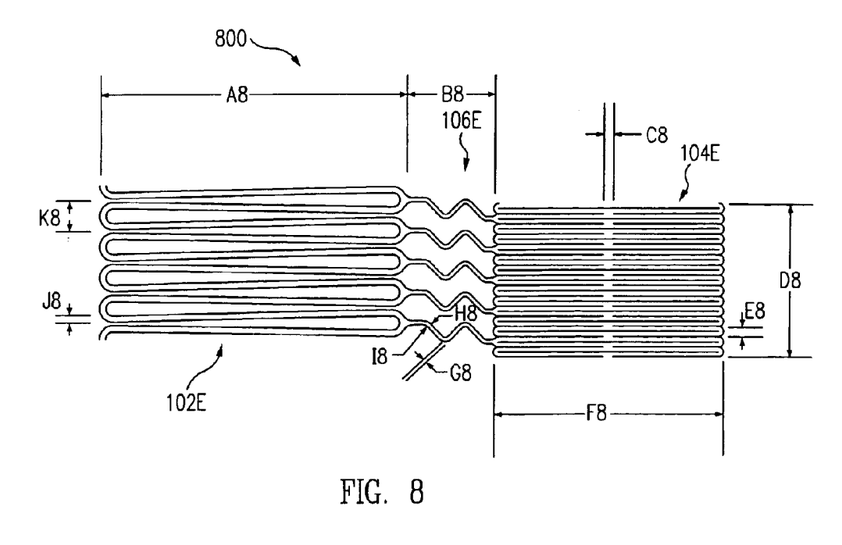

FIG. 8 is a flat layout plan view of a laid flat tube pattern 800 for a single-piece stent showing another embodiment according to the present invention. Referring now to FIG. 8, spring elements 106E consist of sinusoidal shaped connectors extending between upper sinusoidal ring 102E and lower diamond ring 104E. More particularly, each spring element 106E consists of a series of opposing bends. Accordingly, spring elements 106E are sometimes said to be in a sinusoidal pattern.

Illustrative specifications for the various features illustrated in FIG. 8 are set forth below in Table 7.

TABLE 7

| FEATURE | SPECIFICATION | UNIT |
| --- | --- | --- |
| A8 | 0.754 | Inch |
| B8 | 0.254 | Inch |
| C8 | 0.030 | Inch |
| D8 | 0.393 | Inch |

TABLE 7-continued

| FEATURE | SPECIFICATION | UNIT |
|---|---|---|
| E8 | 0.026 | Inch |
| F8 | 0.559 | Inch |
| G8 | 0.010 | Inch |
| H8 | R0.030 | Inch |
| I8 | R0.020 | Inch |
| J8 | 0.022 | Inch |
| K8 | 0.074 | Inch |

The ratio of height A8 of upper sinusoidal ring 102E and height B8 of spring elements 106E is about 3:1. The ratio of height B8 of spring elements 106E and height F8 of lower diamond ring 104E is about 5:11. The ratio of height A8 of upper sinusoidal ring 102E and height F8 of lower diamond ring 104E is about 15:11. The ratio of height A8 of upper sinusoidal ring 102E and height B8 of spring elements 106E and height F8 of lower diamond ring 104E is about 15:5:11.

Figure 9:
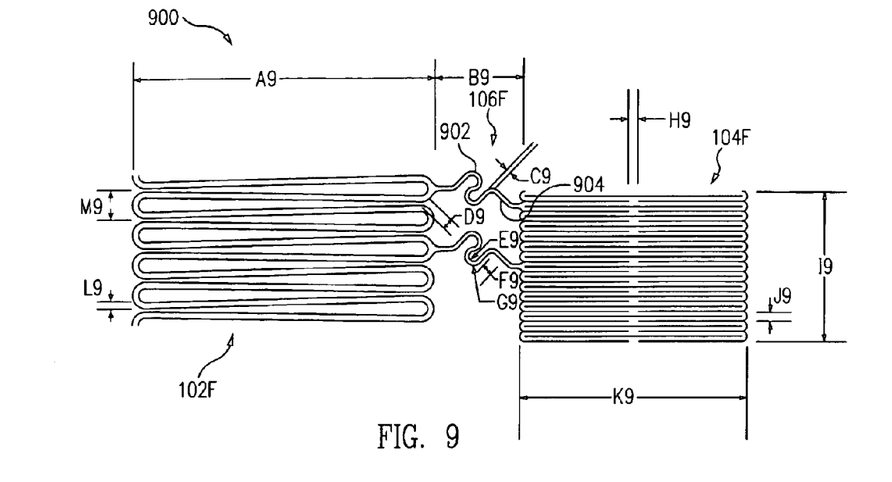

FIG. 9 is a flat layout plan view of a laid flat tube pattern 900 for a single-piece stent showing another embodiment according to the present invention. Referring now to FIG. 9, spring elements 106F consist of offset S-shaped connectors extending between upper sinusoidal ring 102F and lower diamond ring 104F. More particularly, each spring element 106F consists of an S-shaped structure 902 coupled to upper sinusoidal ring 102F and a bent strut 904 coupled to S-shaped structure 902 and lower diamond ring 104F. Accordingly, spring elements 106F are sometimes said to be in an offset S-pattern.

Illustrative specifications for the various features illustrated in FIG. 9 are set forth below in Table 8.

TABLE 8

| FEATURE | SPECIFICATION | UNIT |
|---|---|---|
| A9 | 0.754 | Inch |
| B9 | 0.254 | Inch |
| C9 | 0.010 | Inch |
| D9 | 0.036 | Inch |
| E9 | R0.020 | Inch |
| F9 | 0.022 | Inch |
| G9 | R0.030 | Inch |
| H9 | 0.030 | Inch |
| I9 | 0.393 | Inch |
| J9 | 0.026 | Inch |
| K9 | 0.559 | Inch |
| L9 | 0.022 | Inch |
| M9 | 0.074 | Inch |

The ratio of height A9 of upper sinusoidal ring 102F and height B9 of spring elements 106F is about 7:1. The ratio of height B9 of spring elements 106F and height K9 of lower diamond ring 104F is about 5:11. The ratio of height A9 of upper sinusoidal ring 102F and height K9 of lower diamond ring 104F is about 15:11. The ratio of height A9 of upper sinusoidal ring 102F and height B9 of spring elements 106F and height K9 of lower diamond ring 104F is about 15:5:11.

Figure 10:
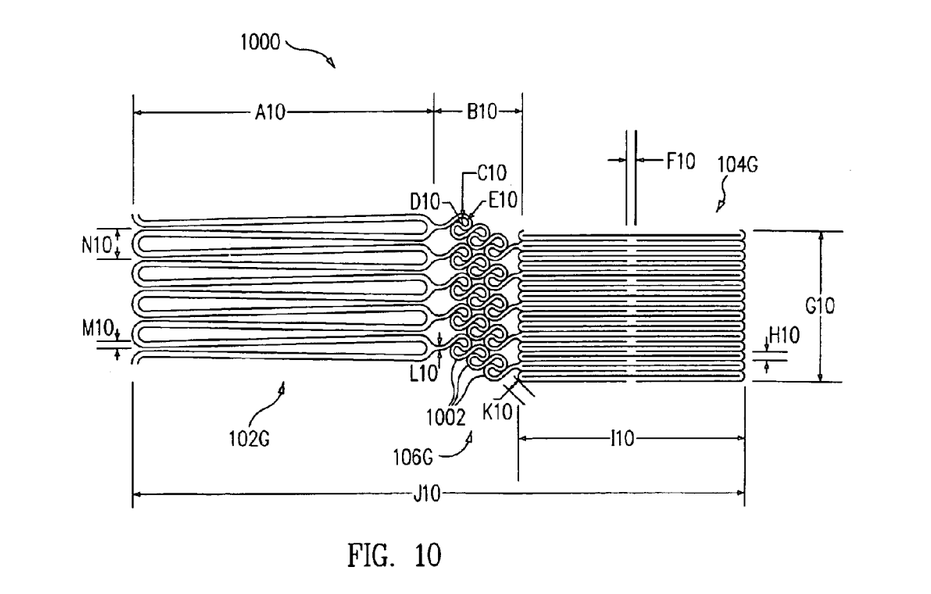

FIG. 10 is a flat layout plan view of a laid flat tube pattern 1000 for a single-piece stent showing another embodiment according to the present invention. Referring now to FIG. 10, spring elements 106G consist of series S-shaped connectors 1002 extending between upper sinusoidal ring 102G and lower diamond ring 104G. More particularly, each spring element 106G consists of a series, e.g., three in the embodiment of FIG. 10, of S-shaped structures 1002. Accordingly, spring elements 106F are sometimes said to be in a series S-pattern.

Illustrative specifications for the various features illustrated in FIG. 10 are set forth below in Table 9.

TABLE 9

| FEATURE | SPECIFICATION | UNIT |
|---|---|---|
| A10 | 0.754 | Inch |
| B10 | 0.266 | Inch |
| C10 | R0.020 | Inch |
| D10 | R0.010 | Inch |
| E10 | R0.015 | Inch |
| F10 | 0.030 | Inch |
| G10 | 0.393 | Inch |
| H10 | 0.026 | Inch |
| I10 | 0.559 | Inch |
| J10 | 1.579 | Inch |
| K10 | 0.036 | Inch |
| L10 | 0.010 | Inch |
| M10 | 0.022 | Inch |
| N10 | 0.074 | Inch |

The ratio of height A10 of upper sinusoidal ring 102G and height B10 of spring elements 106G is about 14:5. The ratio of height B10 of spring elements 106G and height 10 of lower diamond ring 104G is about 10:21. The ratio of height A10 of upper sinusoidal ring 102G and height 110 of lower diamond ring 104G is about 28:21. The ratio of height A10 of upper sinusoidal ring 102G and height B10 of spring elements 106G and height 110 of lower diamond ring 104G is about 21:10:21.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A stent-graft comprising:
   a first sinusoidal ring comprising a series of peaks and valleys;
   a second diamond ring comprising a series of connected diamond shaped structures, a number of said connected diamond shaped structures of said second diamond ring being greater than a number of said valleys, a height of said first sinusoidal ring being greater than a height of said second diamond ring;
   spring elements coupling said first sinusoidal ring to said second diamond ring, said spring elements being coupled to all of said valleys, wherein said first sinusoidal ring, said second diamond ring and said spring elements are integral; and
   a graft material coupled to said second diamond ring only.

2. The stent-graft of claim 1 wherein said stent comprises a memory metal.

3. The stent-graft of claim 2 wherein said memory metal comprises nickel titanium alloy.

4. The stent-graft of claim 1 wherein said spring elements allow said first sinusoidal ring to be bent relative to said second diamond ring.

5. The stent-graft of claim 1 wherein said spring elements are in a straight line pattern.

6. The stent-graft of claim 5 wherein said spring elements comprise straight connectors extending between said first sinusoidal ring and said second diamond ring.

7. The stent-graft of claim 1 wherein said spring elements are in an S-pattern.

8. The stent-graft of claim 7 wherein said spring elements comprise two opposing bends extending between said first sinusoidal ring and said second diamond ring.

9. The stent-graft of claim 1 wherein said spring elements are in a pattern of two S-patterns connected by a strut.

10. The stent-graft of claim 9 wherein said spring elements comprise:

first S-shaped connectors;

second S-shaped connectors; and struts extending between said first S-shaped connectors and said second S-shaped connectors.

11. The stent-graft of claim 10 wherein said struts are straight struts.

12. The stent-graft of claim 10 wherein said struts are wave struts.

13. The stent-graft of claim 1 wherein said spring elements are in a sinusoidal pattern.

14. The stent-graft of claim 13 wherein said spring elements comprise a series of opposing bends.

15. The stent-graft of claim 1 wherein said spring elements are in an offset S-pattern.

16. The stent-graft of claim 15 wherein said spring elements comprise:

S-shaped structures; and bent struts coupled to said S-shaped structures.

17. The stent-graft of claim 1 wherein said spring elements are in a series S-pattern.

18. The stent-graft of claim 17 wherein said spring elements comprise a series of S-shaped structures.

19. The stent-graft of claim 1 wherein there are three of said connected diamond shaped structures for every one of said valleys.

20. The stent-graft of claim 1 wherein a ratio of said height of said first sinusoidal ring to said height of said second diamond ring is about 4:3.

21. The stent-graft of claim 1 wherein a ratio of said height of said first sinusoidal ring to said height of said second diamond ring is about 25:18.

22. The stent-graft of claim 1 wherein a ratio of said height of said first sinusoidal ring to said height of said second diamond ring is about 15:11.

23. The stent-graft of claim 1 wherein a ratio of said height of said first sinusoidal ring to said height of said second diamond ring is about 28:21.

24. A stent-graft comprising:

a first sinusoidal ring comprising a series of peaks and valleys;

a second diamond ring comprising a series of connected diamond shaped structures, a number of said connected diamond shaped structures of said second diamond ring being greater than a number of said valleys, a height of said first sinusoidal ring being greater than a height of said second diamond ring;

means for bending said first sinusoidal ring relative to said second diamond ring, said means for bending being coupled to all of said valleys, wherein said first sinusoidal ring, said second diamond ring and said means for bending are integral; and a graft material coupled to said second diamond ring only.

25. A stent-graft comprising:

a first ring comprising a series of peaks and valleys;

a second ring comprising a series of connected diamond shaped structures, a number of said connected diamond shaped structures of said second ring being greater than a number of said valleys, a height of said first ring being greater than a height of said second ring;

spring elements coupling said first ring to said second ring, wherein said first ring, said second ring and said spring elements are integral; and a graft material coupled to said second ring only.

26. The stent-graft of claim 25 wherein said first ring is a first sinusoidal ring.

27. The stent-graft of claim 26 wherein said second ring is a second diamond ring.

28. The stent-graft of claim 25 further comprising sutures coupling said graft material to said second ring.

29. A method comprising:

applying bending force to a stent-graft to bend a first ring of a stent of said stent-graft relative to a second ring of said stent, said applying causing spring elements between said first ring and said second ring to become distorted, wherein most of said bending occurs in said spring elements without collapse of said first ring and said second ring, wherein said first ring comprising a series of peaks and valleys and said second ring comprising a series of connected diamond shaved structures, a number of said connected diamond shaped structures of said second ring being greater than a number of said valleys, a height of said first ring being greater than a height of said second ring;

providing fixation above the renal arteries with said first ring; and providing sealing at a proximal end of a graft material of said stent-graft with said second ring, said graft material coupled to said second ring only.

30. The method of claim 29 wherein said distorting comprises stretching a first spring element of said spring elements.

31. The method of claim 29 wherein said distorting comprises compressing a first spring element of said spring elements.

32. The method of claim 29 further comprising removing said bending force, said spring elements causing said stent-graft to return to a relaxed state of said stent-graft.

* * * * *